United States Patent [19]

Aebli et al.

[11] 3,940,388
[45] Feb. 24, 1976

[54] TRIAZOLYLSTYRYL TRIAZOLES

[75] Inventors: Horst Aebli, Basel; Fritz Fleck, Botimingen; Horst Schmid, Munchenstein, all of Switzerland

[73] Assignee: Sandoz Ltd., (Sandoz AG), Basel, Switzerland

[22] Filed: Dec. 3, 1973

[21] Appl. No.: 421,002

Related U.S. Application Data

[63] Continuation-in-part of Ser. No. 255,256, May 22, 1972, abandoned.

[30] Foreign Application Priority Data

May 26, 1971 Switzerland.......................... 7685/71

[52] U.S. Cl............................ 260/240.9; 260/42.29
[51] Int. Cl.²........................................ C07D 249/06
[58] Field of Search...... 260/240.9, 240 CA, 240 C, 260/240 D

[56] References Cited
UNITED STATES PATENTS

| | | | |
|---|---|---|---|
| 3,637,673 | 1/1972 | Okubo et al..................... | 260/240.9 |
| 3,689,481 | 9/1972 | Scheuermann et al......... | 260/240 D |
| 3,784,570 | 1/1974 | Schellhammer.......... | 260/240 CA X |

FOREIGN PATENTS OR APPLICATIONS 1,132,314 10/1968 United Kingdom.......... 260/240 CA

*Primary Examiner*—Allen B. Curtis
*Attorney, Agent, or Firm*—Gerald D. Sharkin; Richard E. Vila; Thomas C. Doyle

[57] ABSTRACT

The present invention provides novel compounds of the formula:

in which
$R_1$ signifies hydrogen, fluorine or chlorine atom, a carboxylic or sulphonic acid group or an amide or

I

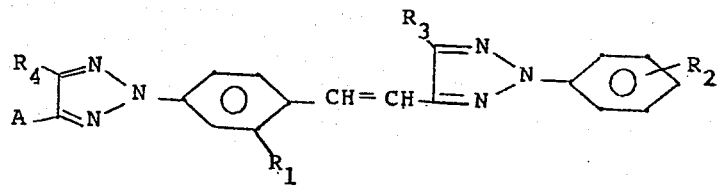

ester thereof, a cyano group or an alkylsulphonyl or arylsulphonyl group, $R_2$ signifies a hydrogen, fluorine or chlorine atom, a cyano group, a phenyl or alkyl radical which may be substituted, a carboxylic or sulphonic acid group or an amide or ester thereof, an alkylsulphonyl or arylsulphonyl group or a benzoxazole group which may be substituted, $R_3$ and $R_4$ independently signify a hydrogen, fluorine or chlorine atom, an alkyl radical of 1 to 6 carbon atoms which may be substituted, a cyano or carboxy group, a carboxylic acid amide or ester group, and $R_4$ may also signify an aryl radical which may be substituted, and A signifies a hydrogen atom or an alkyl or aryl radical which may be substituted or a group of formula II,

B—CH = CH—    II in which B signifies an aryl or heterocyclic radical which may be substituted, and their water soluble sulphonated derivatives.

The compounds are useful as optical brighteners for various organic materials.

8 Claims, No Drawings

TRIAZOLYLSTYRYL TRIAZOLES

This application is a continuation-in-part of co-pending Application Ser. No. 255,256, filed May 22, 1972, and now abandoned.

The invention provides novel triazolylstyryl triazoles. The invention provides compounds of formula I,

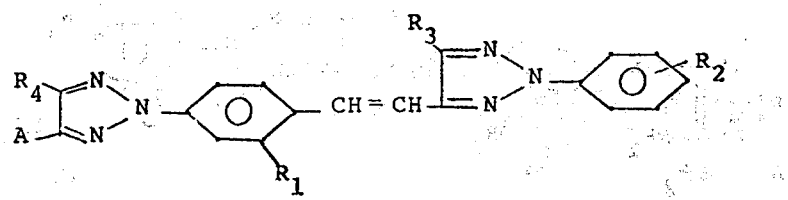

in which
$R_1$ signifies hydrogen, fluorine or chlorine atom, a carboxylic or sulphonic acid group or an amide or ester thereof, a cyano group or an alkylsulphonyl or arylsulphonyl group,
$R_2$ signifies a hydrogen, fluorine or chlorine atom, a cyano group, a phenyl or alkyl radical which may be substituted, a carboxylic or sulphonic acid group or an amide or ester thereof, an alkylsulphonyl or arylsulphonyl group or a benzoxazole group which may be substituted,
$R_3$ and $R_4$ independently signify a hydrogen, fluorine or chlorine atom, an alkyl radical of 1 to 6 carbon atoms which may be substituted, a cyano or carboxy group, a carboxylic acid amide or ester group, and $R_4$ may also signify an aryl radical which may be substituted, and
A signifies a hydrogen atom or an alkyl or aryl radical which may be substituted or a group of formula II,
B — CH = CH —    II
in which B signifies an aryl or heterocyclic radical which may be substituted,
and their water soluble sulphonated derivatives.

The invention also provides a process for the production of compounds of formula I which comprises reacting a hydrazine of formula III,

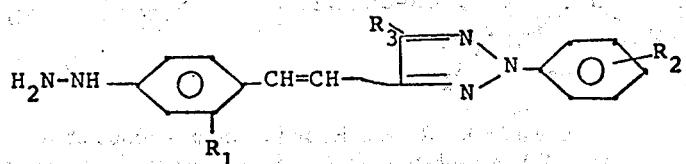

in which $R_1$, $R_2$ and $R_3$ are as defined above, with an iso-nitroso compound of formula IV,

in which one of $Z_1$ and $Z_2$ signifies an oxygen atom and the other Z signifies =N-OR,
in which
R signifies hydrogen or an acyl group, preferably an acetyl group,
and A and $R_4$ are as defined above, and dehydrative cyclization of the reaction product to form the compound of formula I, or by oxidative cyclization to the v-triazole-1-oxide compound and reduction of this to the compound of formula I and in the latter case when $Z_1$ signifies =N-OH and $R_4$ signifies H with optional replacement of the $R_4$ substituent by a chlorine atom before or after reduction of the triazole-N-oxide compound to the corresponding triazole compound, or b. condensing a compound of formula V,

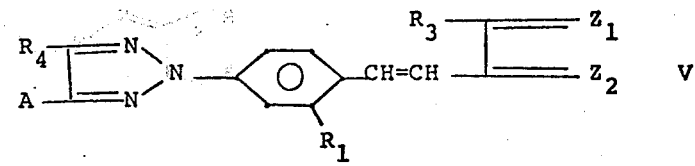

in which $R_1$, $R_3$, $R_4$, A and $Z_1$ and $Z_2$ are as defined above, with a hydrazine of formula VI,

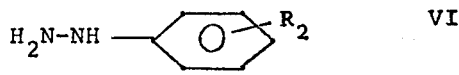

in which $R_2$ is as defined above,
and direct dehydrative cyclization of the product to the compound of formula I or oxidative cyclization to the v-triazole-1-oxide compound and reduction of this to the compound of formula I, and in the latter case, when $Z_1$ signifies =N-OH and $R_3$ signifies hydrogen, with optional replacement of the $R_3$ hydrogen substituent by a chlorine atom before or after reduction of the triazole-N-oxide compound to the corresponding triazole compound, or
c. reacting a compound of formula VII,

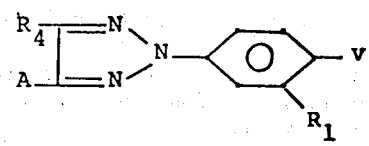 VII with a compound of formula VIII,

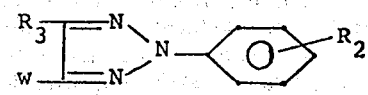 VIII in which formulae VII and VIII, $R_1$ to $R_4$ and A are as defined above, and one of the v and w signifies a —CHO group or a functional derivatives thereof and the other signifies a —CH$_2$-t$_1$ group, in which t$_1$ signifies hydrogen —CN, —COOH, a carboxylic acid ester or amide group —PO(O-alkyl)$_2$, —PO(O-aryl)$_2$,

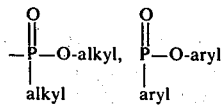

or —P$^+$(aryl)$_3$X
in which alkyl is preferably alkyl lower, e.g. with 1 to 6 carbon atoms, may be substituted, e.g. by methoxy, ethoxy, phenyl or phenoxy, and includes cycloalkyl, e.g. cyclohexyl; aryl is preferably (optionally substituted) phenyl; and X$^\ominus$ is a monovalent anion, e.g. Cl$^\ominus$, Br$^\ominus$, I$^\ominus$, CH$_3$-O-SO$_3{}^\ominus$, C$_2$H$_5$-O-SO$_3{}^\ominus$, CH$_3$-SO$_3{}^\ominus$, with cleavage of the substituent t$_1$ where necessary, or
d. oxidative cyclization of a compound of formula IX,

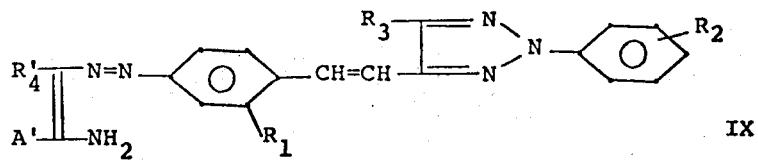 IX in which $R_1$, $R_2$ and $R_3$ are as defined above,
A' signifies an alkyl or aryl radical which may be substituted or a group of formula II as defined above,
R'$_4$ signifies —CN, —COOH or a carboxylic acid amide or ester group,
to form a compound of formula Ia,

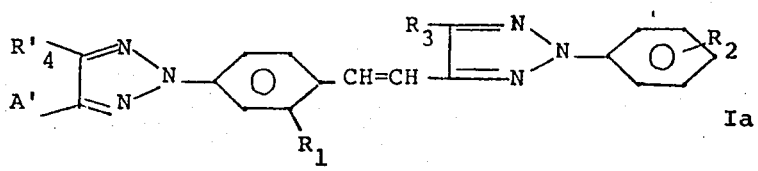 Ia in which $R_1$, $R_2$, $R_3$, R'$_4$ and A' are as defined above, or
e. oxidative cyclization of a compound of formula X,

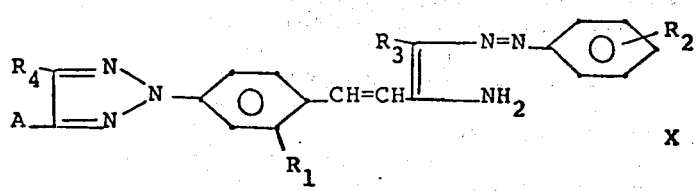 X in which $R_1$, $R_2$, $R_4$ and A are as defined above, and $R_3$ signifies —CN, —COOH or a carboxylic acid ester or amide, to form a compound of formula Ib,

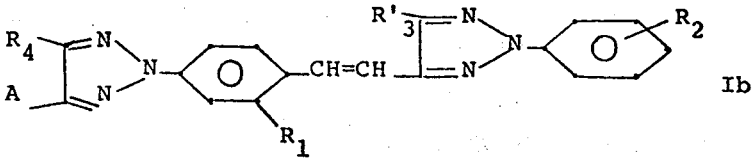 Ib in which $R_1$, $R_2$, R'$_3$, $R_4$ and A are as defined above.
When a substituent $R_1$ to $R_4$ is a carboxylic acid ester group it is preferably an alkylester group of a carboxylic acid which has 1 to 8 carbon atoms in the alkyl radical and may be substituted by alkoxy, phenyl or phenoxy radicals or a cycloalkylester or arylester group of a carboxylic acid, preferably those of the naphthalene, diphenyl and in particular the benzene series. Examples of suitable carboxylic ester groups are the methyl, ethyl, n-propyl, iso-propyl, n-butyl, iso-butyl, n-amyl, iso-amyl, n-hexyl, n-octyl, 2-ethylhexyl, 2-methoxyethyl, 2-ethoxyethyl, 2-n-butoxyethyl, 2-(2'-methoxyethoxy)-ethyl, 2-(2'-ethoxyethoxy)-ethyl, 2-(2'-butoxyethoxy)-ethyl, benzyl, 2-phenylethyl, 2-phenoxyethyl, cyclohexyl, 4-methyl-cyclohexyl, 4-diphenylyl, naphthyl-1, naphthyl-2, phenyl, 2-, 3- and 4-methylphenyl, 2-, 3 and 4-chlorophenyl, 2-and 4-methoxyphenyl, 2- and 4-ethoxyphenyl, 4-fluorophenyl, 2,4- and 2,5-dimethylphenyl-, 4-n-butylphenyl, 4-tert. butylphenyl, 4-tert. amylphenyl and 4-tert. octylphenyl ester groups.

If $R_1$ and/or $R_2$ are sulphonic acid ester groups, the sulphonic acid ester groups corresponding to the aforenamed carboxylic acid ester groups are suitable substituents.

When a substituent $R_1$ to $R_4$ is a carboxylic acid amide group or a substituent $R_1$ or $R_2$ is a sulphonic acid amide group, the amide is preferably a monoalkylamide, dialkylamide, mono- and di-(hydroxyalkyl)-amide, alkoxyalkyl- and alkoxyalkoxyalkylamide, arylamide, aralkyl-, aryloxyalkyl- and cycloalkylamide, N-alkyl- or N-hydroxyalkyl-N-phenylamide group, in which alkyl and hydroxyalkyl may contain, e.g., 1 to 6 or, preferably, 1 to 4 carbon atoms, alkoxyalkyl and alkoxyalkoxyalkyl containing preferably 3 to 6 and 5 to 8 carbon atoms respectively, aryl and aryloxy may be binuclear or, preferably, mononuclear. Specific examples are the following amide groups of carboxylic and sulphonic acids: methyl, ethyl, n-propyl, iso-propyl, n-butyl, sec. butyl, iso-butyl, n-amyl, n-hexyl, iso-amyl, dimethyl, diethyl, di-n-butyl, 2-hydroxyethyl, 2- and 3-hydroxypropyl, 4-hydroxybutyl, di-(2-hydroxyethyl), di-(2-hydroxypropyl)-, 2-methoxyethyl, 2-ethoxyethyl, 2-n-butoxyethyl, 3-methoxypropyl, 4-methoxybutyl, 2-(2'-methoxyethoxy)-ethyl, 2-(2'-ethoxyethoxy)-ethyl, 2-(2'-n-butoxyethoxy)-ethyl, phenyl, 2-, 3- and 4-methylphenyl, 2-, 3- and 4-chlorophenyl, 2- and 4-methoxyphenyl, 2- and 4-ethoxyphenyl, 4-tert. butylphenyl, 4-n-butylphenyl, 2,4- and 2,5-dimethylphenyl, 4-diphenylyl, naphthyl-1, naphthyl-2, N-methyl-N-phenyl, N-ethyl-N-phenyl, N-2-hydroxyethyl-N-phenyl, cyclohexyl, 4-methylcyclohexyl, benzyl, phenylethyl and phenoxyethyl amide groups.

When $R_1$ or $R_2$ signifies an alkylsulphonyl group it may contain, e.g., 1 to 6 carbon atoms (n-propyl-, iso-propyl-, n-butyl-, iso-butyl-, n-amyl-, iso-amyl- or n-hexyl-sulphonyl and in particular methylsulphonyl and ethylsulphonyl). The arylsulphonyl significances of $R_1$ or $R_2$ preferably contain aryl radicals of the benzene series such as phenyl-, methylphenyl- and chlorophenyl-sulphonyl.

When $R_2$ signifies an optionally substituted alkyl radical this may be branched or unbranched, and preferably contains 1 to 18 carbon atoms especially 1 to 8 carbon atoms and may bear as substituents, e.g., halogen atoms, cyano, hydroxyl, alkoxy, aryl or aryloxy groups, preferably of the benzene series and examples of suitable optionally substituted alkyl radicals are methyl, ethyl, n-propyl, iso-propyl, n-butyl, iso-butyl, sec. butyl, tert. butyl, n-amyl, tert. amyl, iso-amyl, sec. amyl, n-hexyl, n-octyl, 2-ethylhexyl, tert. octyl, n-decyl, n-dodecyl, cetyl, stearyl, 2-methoxyethyl, 2-ethoxyethyl, 2-n-butoxyethyl, 3-methoxypropyl, 4-methoxybutyl, 2-hydroxyethyl, 2- and 3-hydroxypropyl, 2-chlorethyl, 2,2-difluorethyl, trifluoromethyl, cyanomethyl, cyanethyl, 2-phenoxyethyl, benzyl, 2-phenylethyl and cumyl.

When $R_2$ signifies an optionally substituted phenyl radical it may be, for example, phenyl, 2-, 3- or 4-methylphenyl, 2-, 3- or 4-chlorophenyl, 2- or 4-methoxyphenyl, 2- or 4-ethoxyphenyl, 4-fluorophenyl, 4-ethyl-, 4-iso-propyl-, 4-tert. butyl-, 4-tert. amyl-, 4-tert. oxtyl-phenyl, 2,4- or 2,5-dimethylphenyl, 2-, 3- or 4-carboxyphenyl, 2-, 3- or 4-cyanophenyl, 2-, 3- or 4-aminocarbonylphenyl, 2-, 3- or 4-methylamino- or 2-, 3- or 4-dimethylamino-carbonylphenyl, 2-, 3- or 4-ethoxy-, n-butoxy-, benzyloxy-, cyclohexyloxy-, phenoxy- or cresoxy-carbonylphenyl, 3- or 4-sulphophenyl, 3- or 4-amino-, methylamino- or dimethylaminosulphonylphenyl, 3- or 4-methoxy-, n-butoxy-, benzyloxy-, cyclohexyloxy-, phenoxy- or cresoxy-sulphonylphenyl.

If $R_2$ signifies a substituted benzoxazole radical, the substituents may be chosen, for example, from alkyl or alkoxy radicals having 1 to 8 carbon atoms which may themselves be substituted, aryl or aryloxy radicals which may themselves be substituted, chlorine or fluorine atoms, cyano groups, sulphonic acid or sulphonamide groups, alkylsulphonyl or arylsulphonyl groups. Examples of alkyl and alkoxy radicals which may themselves be substituted are methyl to octyl, benzyl, 2-phenoxyethyl, methoxy, ethoxy, n-butoxy, n-octyloxy, cyclohexyl etc. Of the aryl and aryloxy radicals, those of the benzene series are especially preferred: phenyl, methylphenyl, chlorophenyl, fluorophenyl, methoxyphenyl, ethoxyphenyl, cyanophenyl, and the corresponding phenoxy compounds.

If the substituents $R_3$ to $R_4$ are alkyl radicals, these contain only 1 to 6 carbon atoms (methyl to hexyl) and may bear the same substituents as given for $R_2$.

Examples of optionally substituted aryl radicals as significances for $R_4$ are the binuclear naphthyl-1, naphthyl-2 and diphenyl-4 radicals and in particular the phenyl radicals described above for $R_2$.

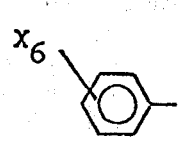

XXI

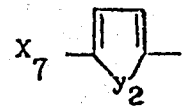

XXII

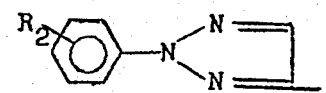

XXIII

XXIV

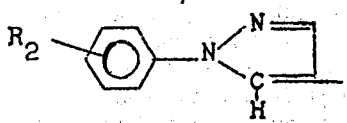

XXV in which $R_2$ is as defined above, and $X_6$ signifies $X_1$ as defined above or an aromatic heterocyclic radical, e.g., a benzoxazole, benzotriazole or naphthotriazole radical, $X_7$ signifies a hydrogen atom, an alkyl radical with 1 to 6 carbon atoms which may be substituted or an aryl radical which may be substituted and which is preferably of the benzene series, $Y_2$ signifies an oxygen or sulphur atom, and the pyridine nucleus in formula XXIV may be substituted.

The condensation step of process variant (a) or (b) may be conveniently effected in an inert organic, preferably polar solvent, e.g. in an aliphatic or aromatic, preferably halogenated or nitrated, hydrocarbon, in an alcohol, ether, glycol, amide, e.g., formamide, dimethyl formamide, dimethyl acetamide, N-methyl pyrrolidone, phosphoric tris-(dimethylamide), in a nitrile, e.g. acetonitrile, in a sulphoxide or sulphone, e.g. dimethyl sulphoxide or tetramethylene sulphone, or in a lower alkanecarboxylic acid, e.g. acetic or propionic acid. Suitable reaction temperatures are from 0° to 100°C, preferably 20° to 60°C. The reaction is preferably effected in the presence of an acid, preferably an organic lower carboxylic acid, e.g. formic, acetic, propionic, butyric, oxalic, tartaric, lactic or citric acid.

The dehydrative cyclization reaction can be conveniently carried out by heating in the presence of an organic solvent and preferably a tertiary base, together with at least the amount of a dehydrating agent necessary for splitting off 1 mol of water.

Examples of suitable dehydrating agents are the halides of phosphoric acid such as phosphorus trichloride, oxychloride and pentachloride, and the halides, amides and, preferably, the anhydrides of carboxylic acids, preferably those anhydrides of the lower fatty acids such as acetic, propionic or butyric acid and mixed anhydrides thereof. Among the carboxylic amides, urea as the diamide of carbonic acid holds a special position. With this dehydrating agent both the hydrazonoximes and their O-acyl derivatives, preferably their O-acetyl derivatives, can be converted into the corresponding compounds of formula I.

The O-acyl derivatives of the hydrazonoximes can also be formed by the reaction of hydrazonoximes with acylating agents, e.g. acetic anhydride, if necessary in the presence of a tertiary base such as pyridine, in accordance with the known methods.

An anhydride of a lower fatty acid is an especially preferred dehydrating agent and is preferably used in excess.

Solvents suitable for the hydrazonoximes and their O-acyl derivatives are those inert solvents which do not affect the dehydrating agents; examples are aromatic and chlorinated hydrocarbons, ethers, ketones, acid amides, sulphoxides and sulphones. Especially valuable solvents are acid amides, sulphoxides and sulphones, e.g. dimethyl formamide, diethyl formamide, dimethyl acetamide, N-methylpyrrolidone, dimethyl sulphoxide, dibutyl sulphoxide, tetramethylene sulphone (sulpholan) and phosphoric tris-(trimethylamide).

Depending on the solubility of the hydrazonoxime, the solvent is usually employed in an amount which is equal to or several times greater than the weight of the hydrazonoxime.

The tertiary base may be used in stoichiometric or catalytic amounts. Of the tertiary bases whose presence promotes the reaction, special mention may be made of diethylaminobenzene, dimethylaminobenzene, quinoline, pyridine, alkylpyridines and technical mixtures of pyridine bases.

The favourable temperature range for the cyclization reaction giving the triazole is 20° to 200°C, in particular from 50° to 175°C. The reaction is preferably carried out stepwise, e.g. first at 80°C, then at 100°C and finally at boiling temperature.

Cyclization to the triazole of formula I can also be accomplished simply by heating in the presence of a carboxylic acid amide, preferably urea, suitably at a temperature of 100° to 210°C, preferably 120° to 175°C. It is not necessary to dry the hydrazonoxime prior to cyclization. The moist hydrazonoxime can be added, for example, to a urea melt. During the heating-up period the water evaporates and cyclization takes place. It is preferred to employ two to twenty times, especially three to fifteen times the amount of urea in relation to the dry amount of the hydrazonoxime. A combination of urea and a lower fatty acid, e.g. acetic acid, is particularly advantageous.

The oxidative cyclization may be effected by the action of a wide variety of oxidizing agents; for this reaction the use of oxidation-stable solvents is advisable. Suitable oxidizing agents include bichromate and hydrogen peroxide in acid, for example acetic acid solution, and potassium ferricyanide in basic solvents such as pyridine and pyridine-water mixtures. A generally employable and preferred process consists in oxidation with a copper (II) salt such as copper (II) sulphate, chloride or acetate in a pyridine-water mixture. The cupric salts can be employed in stoichiometric amounts or in excess of or below the stoichiometric amount. The monovalent copper formed in the reaction can be continuously converted into the divalent stage during the reaction by blowing in air or oxygen.

The reduction of the triazole oxides to the final compounds is carried out in conventional manner, preferably using nascent hydrogen from a base metal and an acid, especially zinc dust in acetic acid, in an acetic acid-water mixture or in a mixture of acetic acid and an inert organic solvent, preferably chlorobenzene. The reaction can be conveniently carried out at temperatures from room temperature to about 150°C, the preferred range being 60° to 130°C. The reduction can also be carried out at a lower temperature, if necessary with a small addition of an inorganic acid, e.g. hydrochloric acid, for acceleration. The salts of reducing acids of sulphur or phosphorus can also be used for reduction.

Simultaneously with reduction of the oxide to the v-triazole ring, treatment of the triazole oxide with hydrogen chloride leads to the introduction of a chlorine atom in the 5-position of this ring adjacent to the N-oxide grouping, when $R_3$ or $R_4$ stand for hydrogen. This reaction is preferably conducted with gaseous hydrogen chloride, which is introduced into a dispersion of the N-triazole oxide in a mixture of water and a water-soluble organic solvent, preferably an alcohol or ether e.g. ethanol, propanol, butanol, methyl glycol, ethyl glycol, ethylene glycol, diethylene glycol or dioxan, at the reflux temperature of the reaction mixture. These chlorine-containing compounds can also be formed by reacting the N-triazole oxide with a chlorinating agent, e.g. sulphuryl chloride, thionyl chloride or phosphoryl chloride, in a solvent inert to halogenation, with subsequent reduction with nascent hydrogen to the 5-chloro-N-triazole compound as described above.

In process variant (c) the reaction of a compound of formula VII with a compound of formula VIII, in which the aldehyde group is present as such or in the form of a derivative, e.g. the oxime, hydrazone, azine or anile, is preferably carried out in the presence of a suitable condensing agent or catalyst, e.g. boric acid, zinc chloride, arylsulphonic acid, an alkali or alkaline-earth metal salt of an arylsulphonamide, acetic anhydride, an alkali metal acetate, piperidine, an alkali or alkaline-earth metal hydroxide or an alkali or alkaline-earth metal alcoholate. Suitable temperatures are from 0° to 200°C, preferably from 20° to 160°C. If $t_1$ stands for hydrogen, the progress of the reaction is assisted if the adjacent benzene nucleus bears a negative substituent, e.g. —CN, —COOH, —SO$_3$H or an optionally substituted ester or amide group of a carboxylic or sulphonic acid. If a radical $t_1$ other than hydrogen is present in the reaction product, it is removed by suitable means, or more exactly is replaced by a hydrogen atom. With a reaction product in which $t_1$ is a COOH group, this removal can be effected, for example, by heating to about 200°C in a solvent of high boiling point, e.g. a tertiary amine such as quinoline; if $t_1$ is a cyano, carboxylic amide or ester group the step is carried out with prior acid or alkaline saponification of this group to the carboxy group. If, however, $t_1$ in the starting product is a phosphorus-containing ester group, this group is replaced by a hydrogen atom during the course of the reaction of the compounds of formulae VII and VIII.

The reaction can be carried out effectively by fusing the reactants, though it is preferred to use an inert solvent, e.g. an aliphatic or aromatic, preferably halogenated hydrocarbon, one of the alcohols, ethers or glycols, an amide such as formamide, dimethyl formamide or acetamide, N-methylpyrrolidone, phosphoric tris-(dimethylamide), acetonitrile, dimethyl sulphoxide, tetramethylene sulphone.

In the above process variants (a), (b) and (c) the reactants are preferably used in approximately equimolar proportions.

The oxidative cyclization of compounds of formulae IX or X in process variants (d) and (e) can be conveniently carried out in the presence of an oxidation-stable organic solvent, such as: hydrocarbons, including halogenated or nitrated hydrocarbons, e.g. benzene, toluene, chlorobenzene, ortho-dichlorobenzene, bromobenzene, nitrobenzene, 1-2-dichlorethane, 1,1,2,2-tetrachlorethane; amides, e.g. dimethyl formamide, dimethyl acetamide, phosphoric tris-(dimethylamide); sulphones, e.g. tetramethylene sulphone; ethers, e.g. methoxybenzene, ethoxybenzene, dioxan, 1,2-dimethoxy- and 1,2-diethoxy-ethane; and tertiary amines, e.g. dimethylamino- and diethylaminobenzene, triethylamine, tri-(n-butyl)-amine, pyridine, picoline, quinoline and mixtures of pyridine bases.

Suitable oxidizing agents include alkali metal hypohalogenites, preferably sodium hypochlorite or hypobromite; inorganic and organic copper (II) compounds such as copper (II) chloride, sulphate, acetate, carbonate and naphthenate, which are employed preferably in the presence of nitrogenous bases such as ammonia, amines such as trimethylamine, ethanolamine, diethanolamine, triethanolamine and pyridine; and air or oxygen in the presence of a copper (II) compound, of which the latter can be employed in catalytic to stoichiometric amounts or in excess.

The oxidative cyclization reaction can be conveniently effected at temperatures ranging from 0° to 150°C, the preferred ranges being from room temperature to 40°C when the oxidizing agent is one of the alkali hypohalogenites and 80° to 130°C for oxidization with a copper compound alone or with oxygen or air in the presence of a copper (II) compound in an amount of, e.g., up to 10% of the stoichiometric amount.

The compounds of formula I may be isolated by the known methods, e.g. by cooling, dilution with a suitable agent, partial or complete evaporation of the solvent or solvents, steam distillation etc., followed by filtration, washing if necessary, and drying and purified in conventional manner.

It will be appreciated that the compounds of formula I may be converted into further compounds by substitution and/or further cyclization. Thus, for example, in a compound of formula I in which one of the substituents is, or has as a substituent, an acid group, such group may be converted into an ester or amide group. Also, for example, a compound of formula I in which A and/or R$_2$ signifies an amide of an o-hydroxyarylamine with a carboxylic or phenylcarboxylic acid radical, may be subjected to dehydrative cyclization to form a compound of formula I in which A and/or R$_2$ is a naphthoxazolyl, benzoxazolyl, naphthoxalylphenyl or benzoxazolylphenyl radical.

To convert water-insoluble triazolyl styryl triazoles of formula I into the corresponding water-soluble sulphonated compounds they can be treated with sulphonating agents, e.g. concentrated sulphuric acid of 90 to 100% strength, weak oleum with an SO$_3$ content of up to about 30%, chlorosulphonic acid or gaseous sulphur trioxide. The temperature may range from 0° to about 100°C, or preferably from 20 to 50°–60°C, and sulphonation is continued until the number of sulphonic acid groups, e.g. 1 to 3, reqquired to impart solubility in water has been introduced. If chlorosulphonic acid or gaseous sulphur trioxide is used, sulphonation proceeds satisfactorily in an inert solvent such as sulphuric acid, ortho-dichlorobenzene or nitrobenzene, while if concentrated sulphuric acid or oleum is chosen the sulphonating agent itself may serve as solvent. The compounds of formula VII in which v signifies —CHO and R$_1$ signifies SO$_3$H can be produced from the 4,4'-bis-4''-phenyl-v-triazolyl-2'']-stilbene-2,2'-disulphonic acids disclosed in British Pat. No. 1,108,416 by cleavage with potassium permangate in aqueous-alkaline medium (see German Patent No. 115,410).

The compounds of formula VIII in which w stands for —CH$_2$-PO=(O-alkyl)$_2$ can be derived from the corresponding compounds bearing a —CH$_2$-Cl group by reaction with a trialkyl phosphite.

The starting compounds of formula IX, as defined above, can be produced, for example, by coupling diazo compounds from amines of formula XXVI,

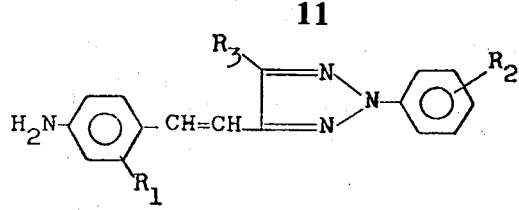

XXVI

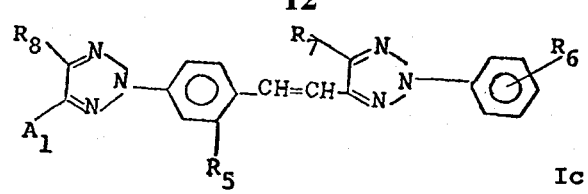

Ic with enamines of formula XXVII

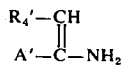

XXVII in which $R_4'$ and $A'$ are as defined above, or with their tautomeric ketimides, e.g. with β-aminocrotonic nitrile, ester or amides or with β-aminocinnamic nitrile, ester or amides.

In an analogous manner, compounds of formula X as defined above can be obtained by coupling diazo compounds from amines of formula XXVIII,

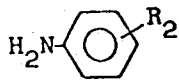

XXVIII in which $R_2$ is as defined above, with enamines of formula XXIX, in which
  $R_5$ signifies the sulphonic acid, sulphonic amide, carboxylic amide or nitrile group,
  $R_6$ signifies a hydrogen or chlorine atom, an alkyl radical having 1 to 4 carbon atoms or the carboxylic amide or nitrile group,
  $R_7$ signifies a hydrogen or chlorine atom or the methyl, hydroxymethyl, chloromethyl or acetoxymethyl group,
  $R_8$ signifies a hydrogen or chlorine atom or the phenyl or methyl group,
  $A_1$ signifies the phenyl, styryl, methylstyryl or nitrilostyryl radical or a radical of formula

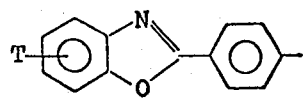

in which T signifies a hydrogen atom or an alkyl radical of 1 to 4 carbon atoms.

An especially preferred group of optical brighteners according to the invention are of formula I d,

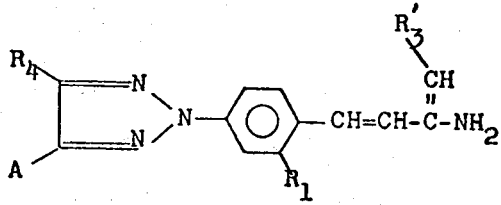

XXIX

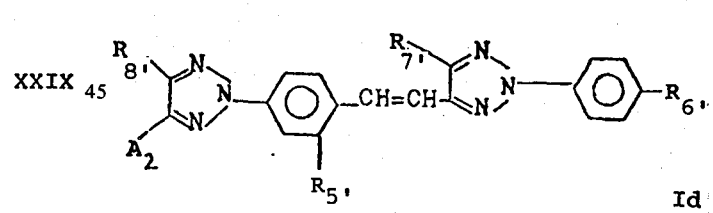

Id in which $R_1$, $R_3'$, $R_4$ and A are as defined above, or with their tautomeric ketimides.

In so far as the production of the starting materials is not described, the compounds are known or may be prepared by known processes, or in a manner analogous to known processes. The new triazolylstyryl triazoles of formula I possess properties suitable for the optical brightening of a wide variety of organic materials and polymeric materials.

A preferred group of optical brighteners according to this invention are those of formula Ic, in which
  $R_9$ signifies the nitrile group or the sulphonic acid group (which may be present as an alkali metal salt, preferably the sodium salt),
  $R_{10}$ signifies a hydrogen atom or the nitrile group,
  $R_{11}$ signifies a hydrogen or chlorine atom or the methyl group,
  $R_{12}$ signifies a hydrogen or chlorine atom or the methyl group,
  $A_2$ signifies the phenyl radical or a radical of formula

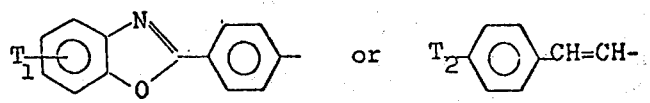

in which

T₁ signifies a hydrogen atom or the methyl or tertiary butyl radical, and

T₂ signifies a hydrogen atom or the methyl or nitrile group.

By "organic materials" are understood natural fibres, e.g. cellulose (paper and cotton) and natural polyamides (wool, silk), and by "polymeric materials" the synthetic and semi-synthetic polymers, e.g. polyesters, polyamides, polyurethanes, polyolefins and optionally, modified polyolefines, polypropylene including polypropylene modifed by the introduction of basic groups), polyvinyl acetate, polyvinyl chloride, polyvinylidene chloride, polyacrylonitrile and modified polyacrylonitrile and acrylonitrile, polystyrene, cellulose (2½) acetate and cellulose triacetate.

The compounds of formula I can be applied to the substrate desired to be brightened by any of the standard exhaust, padding or printing methods, either in the form of solutions in water or an organic solvent or as aqueous dispersions. But they can also be advantageous as brightener additives in spinning solutions and melts, in plastics moulding materials, and in the monomers or prepolymers for the synthesis of polymers. For this latter purpose the water-insoluble triazolylstyryl triazoles of formula I are preferable.

Depending on the method of application, the disclosed compounds are employed in amounts of 0.001 to 0.5 & or preferably 0.01 to 0.2% in relation to the weight of the material. They are suitable for use alone or in combination with other optical brighteners, and may be applied in the presence of surface-active agents, for instance detergents, carriers, and chemical bleaching agents. An effective method of brightening heat-stable synthetic fibres, notably polyester fibres, in fabric form is to pad the selected compound of formula I on the fabric from an aqueous medium containing a surface-active agent and to treat the fabric in dry heat, e.g. at 150°–240°C or preferably 180°–220°C, in accordance with the "thermosol" process.

The disclosed brighteners have a distinct reddish violet to blue fluorescence shade, a high saturation limit, good sublimation fastness and good light fastness. The water-soluble compounds containing sulphonic acid groups can be incorporated in powder, paste or liquid detergents in amounts of, e.g. 0.001 to 0.5% relative to the solid content of the detergent. This group of brighteners may also be used for the optical brightening of cellulosic fibres (cotton, linen, hemp, paper, rayon) and polyamide fibres (wool, silk, hair fibres, polyamide 6, 66, 610, 11 etc.) by the exhaust technique and, in particular, for the optical brightening of nonwovens and carpets by discontinous or continous padding processes.

In the following Examples the parts and percentages are by weight and the temperatures in degrees centigrade. The melting points are uncorrected.

EXAMPLE 1

20 Parts of 4-hydrazino-2-cyano-β-(2'-phenylosotriazolyl)-styrene are added to 48 parts of dimethyl formamide with heating to 60°, on which it goes into solution almost completely. After cooling to 20° with vigorous stirring, 42 parts of 50% acetic acid are added, followed in the course of 1 hour by portions of isonitrosobenzalacetone totalling 13 parts. The mixture is held for a further 3 hours at 20°–25° with thorough stirring and then for 2 hours at 60° until no further hydrazine is indicated. It is cooled slowly, first to room temperature and then in an ice bath to 0°–3°. The yellow precipitate is filtered with suction and washed with ice-cold methanol to give a yellow-brown hydrazonoxime, melting point 195°–220°, which without further purification is suspended in 14 parts of dimethyl formamide at room temperature, with the consecutive addition of 12 parts of pyridine and 5.5 parts of acetic anhydride. The temperature is raised to 80° in 2 hours and in the following 2 hours to 100°. A dark brown solution is formed which is boiled for a further 30 minutes with reflux. It is cooled slowly to 0°–5° and the precipitate filtered with suction, washed with ice-cold methanol and crystallized from chlorobenzene with the aid of bleaching earth. The compound of formula

is obtained in the form of pale yellow crystals, melting point 203°–205°, which fluoresce with a violet shade in chlorobenzene solution (λ max. 365 nm).

EXAMPLE 2

50 Parts of the hydrazonoxime of Example 1 are dissolved in 300 parts of pyridine with heating to 90°. In 45 minutes a solution of 40 parts of copper sulphate pentahydrate, 90 parts of water and 50 parts of pyridine is added dropwise with stirring. The reaction mixture is held for 2½ hours at 90°–100°, then 300 parts of pyridine-water mixture are distilled with vacuum, the mixture cooled and the precipitate filtered with suction. It is washed with 1000 parts of dioxan and then with water until the wash water is colourless, and dried at 60° with vacuum. The yellow-brown triazole-N-oxide formed melts at 229°–233° and corresponds to the formula

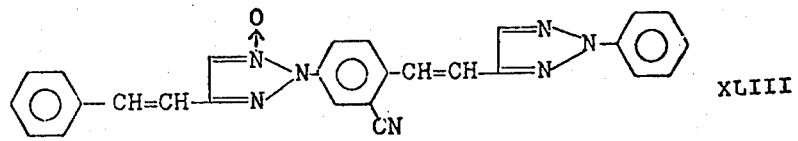

27 Parts of this triazole-N-oxide are dissolved in 300 parts of dioxan and 2 parts of water at 85°. For 5 hours a powerful current of hydrogen chloride gas is directed into the well stirred solution. After a short time it begins to fluoresce and lemon crystals settle out. On completion of the reaction time the batch is cooled and the product filtered with suction. Crystallization from chlorobenzene with the aid of bleaching earth results in lemon crystals with melting point 202°–204°, which fluoresce with a violet shade in chlorobenzene solution and have the formula

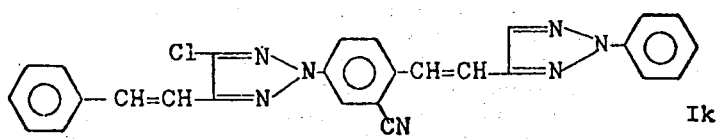

(λ max. in chloroform: 370 nm)

EXAMPLE 3

28 parts of the triazole-N-oxide of formula

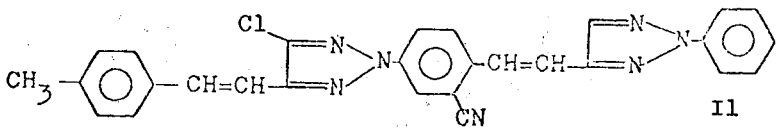

melting point 233°–235°, which can be produced in analogy with the procedure of Examples 1 or 2, are employed for reaction in otherwise complete accordance with Example 2, and lemon crystals, melting point 194°–195°, are obtained which exhibit violet fluorescence in chlorobenzene solution and agree with formula

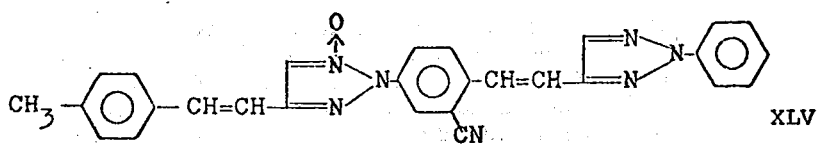

(λ max. in chloroform: 373 nm)

EXAMPLE 4

4.5 Parts of the phosphonic ester of formula

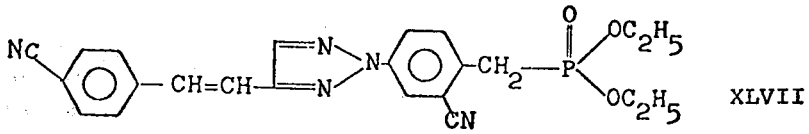

are dissolved with 1.8 parts of 2-phenyl-1,2,3-triazole-4-aldehyde in 40 parts of freshly distilled dimethyl formamide. At 30° a solution of 6 parts of sodium methylate in 12 parts of methyl alcohol is added. The mixture is stirred for 1 hour at 40° and then cooled and set with 20 parts of cold methanol. The yellow precipitate is filtered with suction, washed twice with 10 parts of methanol and crystallized from ortho-dichlorobenzene. The product in the form of pale yellow crystals, melting point 264°–266°, shows blue-violet fluorescence in chlorobenzene solution and has the formula

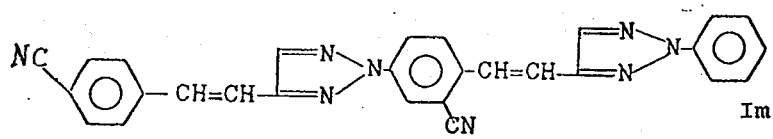

(λ max. in chloroform: 367 nm)

EXAMPLE 5

30 Parts of the phosphonic ester of formula (XLVII) along with 13.5 parts of 2-(4'-cyanophenyl)-4-formyl-1,2,3-triazole are dissolved in 200 parts of distilled dimethyl formamide. A solution of 3.7 parts of sodium methylate in 8 parts of methanol is added at 30° and the batch stirred for 1 hour at this temperature, after which 100 parts of methanol are added, the mixture cooled to 10° and the product isolated by filtration with suction. On recrystallization from ortho-dichlorobenzene, pale yellow crystals with melting point 317°–319° are obtained, which fluoresce with a blue-violet shade in chlorobenzene solution and corresponds to the formula

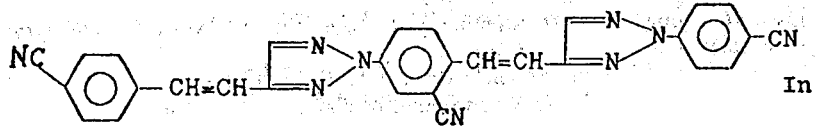

(λ max. in chloroform: 369 nm)

The phosphonic ester of formula (XLVII) is formed as follows. A mixture of 8 parts of 2-(3'-cyano-4'-methyl)-4-formyl-1,2,3-triazole and 9.5 parts of 4cyanobenzylphosphonic diethylester in 50 parts of dry dimethyl formamide is set at room temperature with 8 parts of a 30% solution of sodium methylate in methanol. It is reacted for 1 hour at 40° with stirring and after the addition of 10 parts of methanol is cooled to 10°. The product is isolated by filtration with suction and vacuum dried at 60°. Almost white, needle-shaped crystals are obtained in a yield of 11 parts, which following recrystallization from chlorobenzene melt at 233°–235°. They are of formula

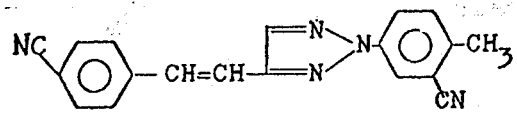

3.1 Parts of the crystalline product are suspended in 100 parts of dry carbon tetrachloride, set for reaction with 2 parts of N-bromosuccinimide and 0.1 part of benzoyl peroxide and reacted for 8 hours with reflux. The precipitated succinimide is filtered off, the filtrate condensed by evaporation and the residue recrystallized from toluene. 4 Parts of the resulting bromomethyl compound, melting point 114°–118°, are converted with triethyl phosphite into the phosphonic diethyl ester of formula (XLVII), crude melting point 210°–220°, following the known method of Michaelis-Arbusov (A. Michaelis, Liebigs Ann. Chem. 326, (1903), 129).

Following the procedure of Example 1 and employing appropriate starting materials in approximately equivalent amounts, the compounds in the following Table III, and which agree with the formula

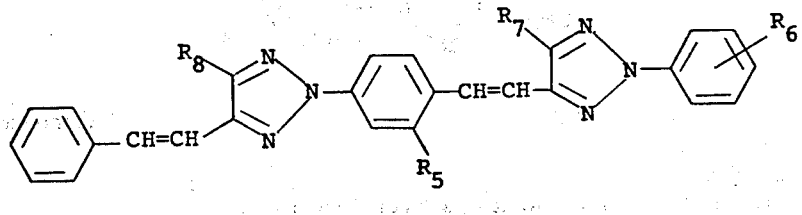

may be produced.

TABLE III

| Ex. No. | $R_5$ | $R_6$ | $R_7$ | $R_8$ | Fluorescence shade in chlorobenzene |
|---|---|---|---|---|---|
| 6 | —SO$_2$NH$_2$ | —Cl | —CH$_3$ | H | Red violet |
| 7 | —CONH$_2$ | —CH$_3$ | —CH$_2$OH | H | " " |
| 8 | —CN | —CONH$_2$ | —Cl | H | " " |
| 9 | —CN | H | —CH$_2$OCOCH$_3$ | H | Bluish violet |
| 10 | —CONH$_2$ | CH$_3$ C CH$_3$ CH$_3$ | —CH$_2$OH | H | Red violet |
| 11 | —CN | H | H | CH$_3$ | Violet |

APPLICATION EXAMPLE A

A solution of 0.005 parts of the compound of formula

L

I j in a plasticizer is blended with 100 parts of moulding material consisting of 65 parts of polyvinyl chloride and 35 parts of a plasticizer, e.g. dioctyl phthalate, and containing 2%, relative to the polymer content, of a stabilizer. The material is worked on a roll mill for 10 minutes at 150°–160° and extruded as film. If opaque film is desired, 2.5% titanium dioxide is incorporated in the material before processing. The films have a superior appearance to comparative films containing no brightener additive.

What is claimed is:

1. A compound of formula

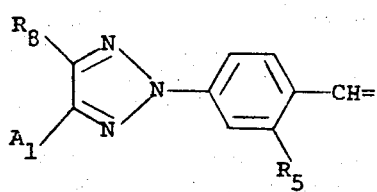

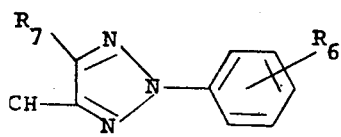

in which
  $R_5$ signifies a sulphonic acid, sulphonic amide, carboxylic amide or nitrile group,
  $R_6$ signifies a hydrogen or chlorine atom, an alkyl radical of 1 to 4 carbon atoms or a carboxylic amide or nitrile group,
  $R_7$ signifies a hydrogen or chlorine atom, or a methyl, hydroxymethyl or acetoxymethyl group,
  $R_8$ signifies a hydrogen or chlorine atom or a methyl group, and
  $A_1$ signifies a styryl, methylstyryl or nitrilostyryl radical,
and water soluble sulphonates thereof.

2. A compound according to claim 1 which in sulphonate form contains 1 to 3 sulphonic acid groups.

3. A compound of claim 1, of formula

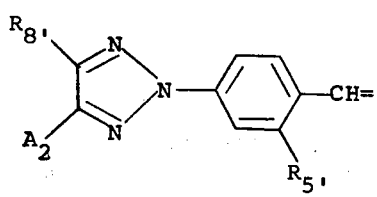

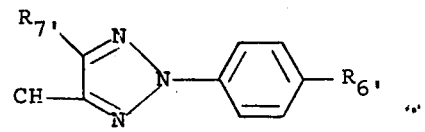

in which
  $R_5'$ signifies a sulphonic acid group or nitrile group,
  $R_6'$ signifies a hydrogen atom or a nitrile group,
  $R_7'$ signifies a hydrogen atom or chlorine atom or a methyl group,
  $R_8'$ signifies a hydrogen or chlorine atom or a methyl group, and
  $A_2$ signifies a styryl, 4-methylstyryl or 4-cyanostyryl group,
and their water soluble sulphonates.

4. A compound of claim 3, of formula

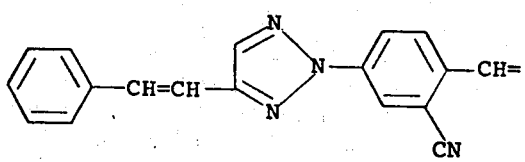

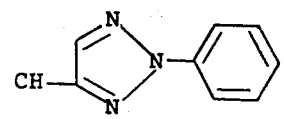

5. A compound of claim 3, of formula

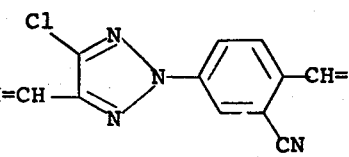

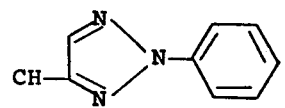

6. A compound of claim 3, of formula

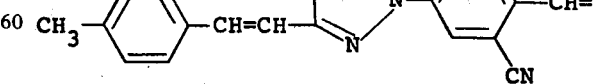

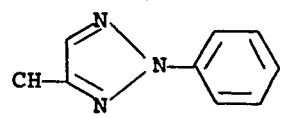

7. A compound of claim 3, of formula
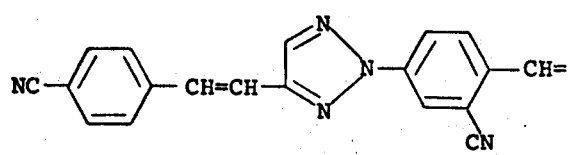
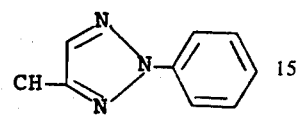
8. A compound of claim 3, of formula
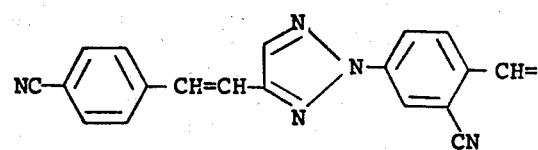
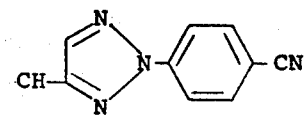
* * * * *